(12) United States Patent
Kalman (10) Patent No.: US 10,537,574 B2
(45) Date of Patent: Jan. 21, 2020

(54) USE OF KINASE INHIBITORS TO MANAGE TUBERCULOSIS AND OTHER INFECTIOUS DISEASES

(71) Applicant: Emory University, Atlanta, GA (US)

(72) Inventor: Daniel Kalman, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/760,978

(22) PCT Filed: Sep. 16, 2016

(86) PCT No.: PCT/US2016/052061
§ 371 (c)(1),
(2) Date: Mar. 16, 2018

(87) PCT Pub. No.: WO2017/049036
PCT Pub. Date: Mar. 23, 2017

(65) Prior Publication Data
US 2018/0250299 A1   Sep. 6, 2018

Related U.S. Application Data

(60) Provisional application No. 62/219,478, filed on Sep. 16, 2015.

(51) Int. Cl.
*A61K 31/506* (2006.01)
*A61P 31/06* (2006.01)
*A61K 45/06* (2006.01)

(52) U.S. Cl.
CPC ............ *A61K 31/506* (2013.01); *A61P 31/06* (2018.01); *A61K 45/06* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 8,268,809 B2 | 9/2012 | Kalman | |
| 8,551,723 B2 | 10/2013 | Zondlo | |
| 8,765,777 B2 * | 7/2014 | Kalman | ............... A61K 31/496 514/275 |
| 2011/0281867 A1 | 11/2011 | Kalman | |
| 2012/0302565 A1 | 11/2012 | Kalman | |
| 2015/0238488 A1 | 8/2015 | Xu | |
| 2018/0250299 A1 | 9/2018 | Kalman | |

FOREIGN PATENT DOCUMENTS

| | | |
|---|---|---|
| WO | 2005072826 | 8/2005 |
| WO | 2012011917 | 1/2012 |
| WO | 2014022382 | 2/2014 |

OTHER PUBLICATIONS

Napier, dissertation, Emory University, Atlanta, GA, 2013, 165 pages (CAS SciFinder abstract).*
Napier et al., Future Microbiology (2012), 7(4), pp. 431-435.*
Bruns et al., Journal of Immunology (2012), 189(8), pp. 4069-4078 (labeled pp. 1-10).*
Napier et al., Cell Host & Microbe (2011), 10(5), pp. 475-485.*
Napier et al., Cell Host & Microbe (2011), 10(6), pp. 635.*
Napier, dissertation, Emory University, Atlanta, GA, 2013, 164 pages.*
Daniels et al. Tuberculosis complicating imatinib treatment for chronic myeloid leukaemia, Eur Respir J 2009; 33: 670-672.
Hawn et al. New tricks for old dogs: countering antibiotic resistance in tuberculosis with host-directed therapeutics, Immunol Rev. 2015, 264(1): 344-362.
Napier et al. Low Doses of Imatinib Induce Myelopoiesis and Enhance Host Anti-microbial Immunity, 2015, PLoS Pathog 11(3): e1004770.
Wallis et al. Advancing host-directed therapy for tuberculosis, Nat Rev Immunol. 2015, 15(4):255-63.

* cited by examiner

*Primary Examiner* — Brian J Davis
(74) *Attorney, Agent, or Firm* — Emory Patent Group (57) ABSTRACT

This disclosure relates to the use of kinase inhibitor to treat or prevent infectious diseases such as tuberculosis. In certain embodiments, this disclosure relates to treating or preventing an infectious disease comprising administering an effective amount of a kinase inhibitor or other compound disclosed herein to a subject in need thereof. In certain embodiments, the disclosure relates to methods of treating or preventing tuberculosis comprising administering a kinase inhibitor to a subject in need thereof. In certain embodiments, the subject is diagnosed with *Mycobacterium tuberculosis* (Mtb) that is resistant to multiple antibiotic agents.

19 Claims, 3 Drawing Sheets

USE OF KINASE INHIBITORS TO MANAGE TUBERCULOSIS AND OTHER INFECTIOUS DISEASES

CROSS-REFERENCE TO RELATED APPLICATIONS

This application is the National Stage of International Application No. PCT/US2016/052061 filed Sep. 16, 2016, which claims the benefit of priority to U.S. Provisional Application No. 62/219,478 filed Sep. 16, 2015. The entirety of each of these applications is hereby incorporated by reference for all purposes.

STATEMENT REGARDING FEDERALLY FUNDED RESEARCH

This invention was made with government support under Grant 1UH2AI122320-01 awarded by NIH. The government has certain rights in the invention.

BACKGROUND

Although curable, tuberculosis (TB) still continues to be a global health problem. TB is caused by a bacterium, known as *Mycobacterium tuberculosis* (Mtb), which typically attacks the lungs; however, it can also damage other organs, such as the kidneys, brain, and liver. TB is spread in the air and transmitted to uninfected individuals when an infected individual, coughs, sneezes, and/or talks. Multiple drug-resistant (MDR) strains of TB infections have developed. Thus, there is a need to identify improved treatments.

Bruns et al. report abelson tyrosine kinase controls phagosomal acidification required for killing of *Mycobacterium tuberculosis* in human macrophages. J. Immunol 2012; 189(8): 4069-78. See also Wallis et al. Nat Rev. Immunol. 2015, 15:255-263 and Chandra, P. et al. mSphere 2016, 1(2):e00043-15.

Daniels et al. report that imatinib (Gleevec) increases the susceptibility of patients to become infected with TB. Eur. Respir J. 2009, 33(3): 670-72.

Naiper et al. report imatinib-sensitive tyrosine kinases regulate mycobacterial pathogenesis and represent therapeutic targets against tuberculosis. Cell Host Microbe. 2011, 10(5): 475-485. See also Napier et al. Low Doses of Imatinib Induce Myelopoiesis and Enhance Host Anti-microbial Immunity. PLoS Pathog, 2015, 11(3): e1004770. See also WO2005072826.

References cited herein are not an admission of prior art.

SUMMARY

This disclosure relates to the use of kinase inhibitor to treat or prevent infectious diseases such as tuberculosis. In certain embodiments, this disclosure relates to treating or preventing an infectious disease comprising administering an effective amount of a kinase inhibitor or other compound disclosed herein to a subject in need thereof. In certain embodiments, the disclosure relates to methods of treating or preventing tuberculosis comprising administering a kinase inhibitor to a subject in need thereof. In certain embodiments, the subject is diagnosed with *Mycobacterium tuberculosis* (Mtb) that is resistant to multiple antibiotic agents.

In certain embodiments, the subject is diagnosed with *Mycobacterium tuberculosis* (Mtb) that is resistant to a combination of 2, 3, or more antibiotic agents. In certain embodiments, the protein kinase inhibitor is imatinib administered in the amount of about 50 to 100 mg per day or 50 to 150 mg per day or 25 to 75 mg per day.

In certain embodiments, the subject is diagnosed with or exhibiting symptoms of an active tuberculosis infection. In certain embodiments, administration prevents reactivation of a latent tuberculosis infection. In certain embodiments, the subject is resistant to treatment of tuberculosis with rifampicin.

In certain embodiments, imatinib is administered in combination with an antibiotic and/or antiviral agent. In certain embodiments, a combined pharmaceutical product is contemplated.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

The term "subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein the term "Imatinib" refers to the compound N-(4-methyl-3-((4-(pyridin-3-yl)pyrimidin-2-yl)amino)phenyl)-4-((4-methylpiperazin-1-yl)methyl)benzamide or salts thereof. A preferred salt is the mesylate salt, but the substitution of other salts are contemplated. As used herein the expression "mg/kg/day" refers to the weight of imatinib mesylate, or an equivalent molar amount of an alternative salt, per kilogram weight of the subject that is to receive the drug per daily administration. As used herein the expression "administered in the amount of X to Y mg per day" refers to the minimum and maximum amounts respectively the subject is to receive in a calendar day. For example "administered in the amount of 50 to 100 mg per day", does not encompass administering more than 100 mg per day, e.g. two 100 mg administrations in one day to total 200 mg. Similarly "administered in the amount of 50 to 100 mg per day", does encompass administering more than 50 mg per day, e.g. three 25 mg administrations in one day to total 75 mg.

As used herein the expression of an administration "in combination with" a drug refers to two drugs which are administered in a manner such that substantial amounts of both of the drugs are circulating at the same time. Administration may be at the same time in the same pharmaceutical product or one after the other in separate formulations. Administrating may be delayed compared to the other as long as the half-life of the administration provides substantial overlapping presence of both of the drug in the circulatory system.

Use to Treat Tuberculosis and Other Infectious Diseases

The greatest need to address TB infections is primarily due to the development of multiple drug-resistant (MDR) strains. Once MDR-TB occurs, second line drugs used often have more side effects, the treatment lasts longer and cost more than first-line drugs. The emergence of MDR-TB and the limitation with current treatments have driven for the development of novel therapeutics to address MDR-TB.

It has been identified that one approach to treat MDR-TB utilized Gleevec (imatinib), a protein tyrosine kinase inhibitor that is often used to treat patients that suffer from chronic myeloid leukemia (CML). One feature of MDR-TB pathogenesis is that it has an ability to replicate and survive in phagocytic cells. *Mycobacterium* use intracellular protein kinases, such as Abl for entry and survival in macrophages. In vivo studies with animals infected with *mycobacterium* indicated that Gleevec (imatinib) not only reduced bacterial load in macrophages, but also reduced the amount of granulomatous lesions within the liver. Imatinib is effective against first-line (rifampicin) resistant strains. Overall, these findings suggest that imatinib is efficacious and can be used in combination with treatments for TB. Contemplated combination include: oral agents such as pyrazinamide, ethambutol, rifabutin; injectable agents such as kanamycin, amikacin, capreomycin, streptomycin; fluoroquinolones such as levofloxacin, moxifloxacin, ofloxacin; and other agents such as para-aminosalicylic acid, cycloserine, terizidone, thionamide, protionamide, clofazimine, linezolid, amoxicillin/clavulanate, thioacetazone, imipenem/cilastatin, isoniazid, and clarithromycin. A combination with delamanid, Bedaquiline, or a combination of pretomanid and moxifloxacin and pyrazinamide is contemplated.

In certain embodiments, this disclosure relates to treating or preventing an infectious disease comprising administering an effective amount of a kinase inhibitor or other compound disclosed herein to a subject in need thereof. In certain embodiments, the disclosure relates to methods of treating or preventing tuberculosis comprising administering a kinase inhibitor to a subject in need thereof. In certain embodiments, the subject is at risk of, exhibiting symptoms of or, diagnosed with and active or latent *Mycobacterium tuberculosis* (Mtb) infection.

In certain embodiments, the subject is diagnosed with *Mycobacterium tuberculosis* (Mtb) that is resistant to multiple antibiotic agents. In certain embodiments, the subject is diagnosed with *Mycobacterium tuberculosis* (Mtb) that is resistant to a combination of 2, 3, or more antibiotic agents. In certain embodiments, the protein kinase inhibitor is imatinib administered in the amount of about 50 to 100 mg per day or 50 to 150 mg per day or 25 to 75 mg per day.

In certain embodiments, the imatinib is administered in amount of 50 to 150 mg per day.

In certain embodiments, the imatinib is administered in amount of 50 to 175 mg per day.

In certain embodiments, the imatinib is administered in amount of 50 to 200 mg per day.

In certain embodiments, the imatinib is administered in amount of 50 to 225 mg per day.

In certain embodiments, the imatinib is administered in amount of 25 to 100 mg per day.

In certain embodiments, the imatinib is administered in amount of 25 to 150 mg per day.

In certain embodiments, the imatinib is administered in amount of 25 to 175 mg per day.

In certain embodiments, the imatinib is administered in amount of 25 to 200 mg per day.

In certain embodiments, the imatinib is administered in amount of 25 to 225 mg per day.

In certain embodiments, imatinib is administered in an amount of 0.1 to 1.0 mg/kg/day.

In certain embodiments, imatinib is administered in an amount of 0.2 to 1.0 mg/kg/day.

In certain embodiments, imatinib is administered in an amount of 0.3 to 1.0 mg/kg/day.

In certain embodiments, imatinib is administered in an amount of 0.4 to 1.0 mg/kg/day.

In certain embodiments, imatinib is administered in an amount of 0.5 to 1.0 mg/kg/day.

In certain embodiments, imatinib is administered in an amount of 0.1 to 0.75 mg/kg/day.

In certain embodiments, imatinib is administered in an amount of 0.2 to 0.75 mg/kg/day.

In certain embodiments, imatinib is administered in an amount of 0.3 to 0.75 mg/kg/day.

In certain embodiments, imatinib is administered in an amount of 0.4 to 0.75 mg/kg/day.

In certain embodiments, imatinib is administered in an amount of 0.5 to 0.75 mg/kg/day.

In certain embodiments, imatinib is administered in an amount of 0.1 to 0.5 mg/kg/day.

In certain embodiments, imatinib is administered in an amount of 0.2 to 0.5 mg/kg/day.

In certain embodiments, imatinib is administered in an amount of 0.3 to 0.5 mg/kg/day.

In certain embodiments, imatinib is administered in an amount of 0.4 to 0.5 mg/kg/day.

In certain embodiments, imatinib is administered in an amount of 0.5 to 0.5 mg/kg/day.

In certain embodiments, imatinib is administered in an amount of 0.01 to 0.5 mg/kg/day.

In certain embodiments, imatinib is administered in an amount of 0.02 to 0.5 mg/kg/day.

In certain embodiments, imatinib is administered in an amount of 0.03 to 0.5 mg/kg/day.

In certain embodiments, imatinib is administered in an amount of 0.04 to 0.5 mg/kg/day.

In certain embodiments, imatinib is administered in an amount of 0.05 to 0.5 mg/kg/day.

In certain embodiments, imatinib is administered in an amount of 0.06 to 0.5 mg/kg/day.

In certain embodiments, imatinib is administered in an amount of 0.07 to 0.5 mg/kg/day.

In certain embodiments, imatinib is administered in an amount of 0.08 to 0.5 mg/kg/day.

In certain embodiments, imatinib is administered in an amount of 0.09 to 0.5 mg/kg/day.

In certain embodiments, imatinib is administered in an amount of 0.1 to 2.0 mg/kg/day.

In certain embodiments, imatinib is administered in an amount of 0.2 to 2.0 mg/kg/day.

In certain embodiments, imatinib is administered in an amount of 0.3 to 2.0 mg/kg/day.

In certain embodiments, imatinib is administered in an amount of 0.4 to 2.0 mg/kg/day.

In certain embodiments, imatinib is administered in an amount of 0.5 to 2.0 mg/kg/day.

In certain embodiments, the administration is consecutively daily administration for 2, 3, 4, 5, 6, 7, 8, 9, 10, 11, 12, 13, or 14 days which may be exact or for more day.

In certain embodiments, the administration is consecutively daily administration that does not exceed 10, 11, 12, 13, 14, 15, 20, 25, 30, 35, or 40 days.

In certain embodiments, the subject is diagnosed with or exhibiting symptoms of an active tuberculosis infection.

In certain embodiments, administration prevents reactivation of a latent tuberculosis infection.

In certain embodiments, the subject is resistant to treatment of tuberculosis with rifampicin.

In certain embodiments, imatinib is administered in combination with an antibiotic or antiviral agent.

In certain embodiments, the antibiotic is ethambutol, isoniazid, pyrazinamide, rifabutin, rifampin, rifapentine, amikacin, capreomycin, cycloserine, ethionamide, levofloxacin, moxifloxacin, para-aminosalicylic acid, streptomycin, or combinations thereof.

In certain embodiments, the combination is isoniazid, pyrazinamide, and rifampin, or a combination of isoniazid and rifampin.

In certain embodiments, the antibiotic is not rifampicin.

In certain embodiments, the subject is diagnosed with HIV.

In certain embodiments, imatinib is administered in combination with an antiviral agent.

In certain embodiments, the antiviral agent is nucleoside reverse transcriptase inhibitor (NRTI) such as abacavir, didanosine, emtricitabine, lamivudine, stavudine, tenofovir disoproxil fumarate, zidovudine, or combinations thereof.

In certain embodiments, the antiviral agent is non-nucleoside reverse transcriptase inhibitor (NNRTI) such as efavirenz, etravirine, nevirapine, rilpivirine or combinations thereof.

In certain embodiments, the antiviral agent is a protease inhibitor such as atazanavir, darunavir, fosamprenavir, indinavir, nelfinavir, ritonavir, saquinavir, tipranavir or combinations thereof.

In certain embodiments, antiviral agent is a combination of abacavir and lamivudine, or a combination of abacavir, dolutegravir, and lamivudine, or a combination of abacavir, lamivudine, and zidovudine, or a combination of atazanavir and cobicistat, or a combination of darunavir and cobicistat, or a combination of efavirenz, emtricitabine, and tenofovir disoproxil fumarate, or a combination of elvitegravir, cobicistat, emtricitabine, and tenofovir alafenamide fumarate, or a combination of elvitegravir, cobicistat, emtricitabine, and tenofovir disoproxil fumarate, or a combination of emtricitabine, rilpivirine, and tenofovir alafenamide, or a combination of emtricitabine, rilpivirine, and tenofovir disoproxil fumarate, or a combination of emtricitabine and tenofovir alafenamide, of a combination of emtricitabine and tenofovir disoproxil fumarate, or a combination of lamivudine and zidovudine, or a combination of lopinavir and ritonavir.

In certain embodiments, imatinib is administered in combination with bedaquiline.

In certain embodiments, the kinase inhibitor is a tyrosine kinase inhibitor such as imatinib, gefitinib, erlotinib, sunitinib, nilotinib, dasatinib, bosutinib, ponatinib and cabozantinib.

In certain embodiments, the infectious disease is bacteria such as *Escherichia coli, Pseudomonas, Salmonella, Shigella, Helicobacter, Anaplasma, Chlamydia*, pathogenic mycobacteria, such as *Mycobacterium tuberculosis* and *Mycobacterium marinum*.

In certain embodiments, the infectious disease is a virus such as a filovirus, HIV, Coxsackie virus, Kaposi sarcoma virus, Polyomaviruse, and orthopoxviruse.

In certain embodiments, the infectious disease is a human parasite *Leishmania*.

Formulations

In certain embodiments, this disclosure contemplates imatinib formulated in a pharmaceutical composition that contains any of the other antibiotics or antiviral agents disclosed herein providing a combined pharmaceutical product.

In certain embodiments, the combined pharmaceutical product contains 25, 50, 75, 100, 125, 150, 175, or 200 mg of imatinib or more but less than 50, 100, 150, or 250 mg.

In certain embodiments, the combined pharmaceutical product contains 10, 20, 30, 40, 50, 60, 70, 80, 90, 100, 110, 120, 130, 140, 150, 160, 170, 180, 190, or 200 mg of imatinib or more but less than 50, 100, 150, or 250 mg.

Pharmaceutical compositions comprising a combined pharmaceutical product disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se.

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778; 6,369,086; 6,369,087; and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound(s) to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing.

Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compounds can be administered in the same dosage form or in separate dosage forms with one or more other active agents.

Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride or sodium citrate, may also be added.

Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. Such a liquid formulation may be administered directly or filled into a soft gelatin capsule.

The pharmaceutical compositions of the application may be in the form of a sterile injectable preparation. Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

EXAMPLES

Imatinib Induces Translocation of Mtb within Infected Macrophages

Imatinib is believed to be effective at doses far lower than the dose used for CIVIL, around 50-100 mg QD oral dosing compared to 400 mg QD for CIVIL. Experiments indicate that the drug reaches a peak concentration in the micromolar range within 6 hrs of administration, which induces translocation of Mtb within infected innate cells (e.g. macrophages) from the phagosome into the lysosome (which depends on Abl), and in so doing enhances bacterial killing and antigen presentation. As the concentration in the blood declines to ~100 nM over the next 18 hours, a second mechanism becomes apparent. This one depends on partial inhibition of c-Kit and is initiated in the bone marrow. Here, the drug encourages the stem cells to divide and differentiate along the myeloid lineage, a process called myelopoiesis. This causes an increase in the numbers of innate immune cells in the blood and organs, which can engulf Mtb. This low dose effect mimics the emergency response, to infection, and innate process that is inhibited by Mtb. The end result of dosing in this way is to produce more innate cells with better killing potential.

Administration to Rhesus Macaques.

Figure 1:
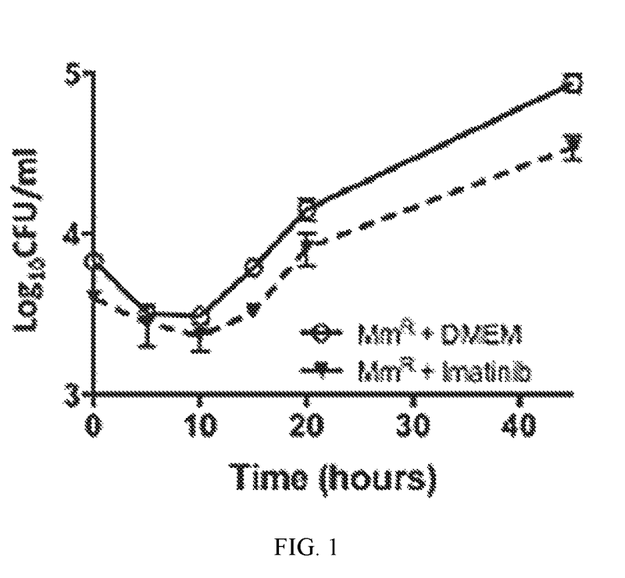
FIG. 1 shows data indicating imatinib decreases bacterial load in macrophages.
Figure 2:
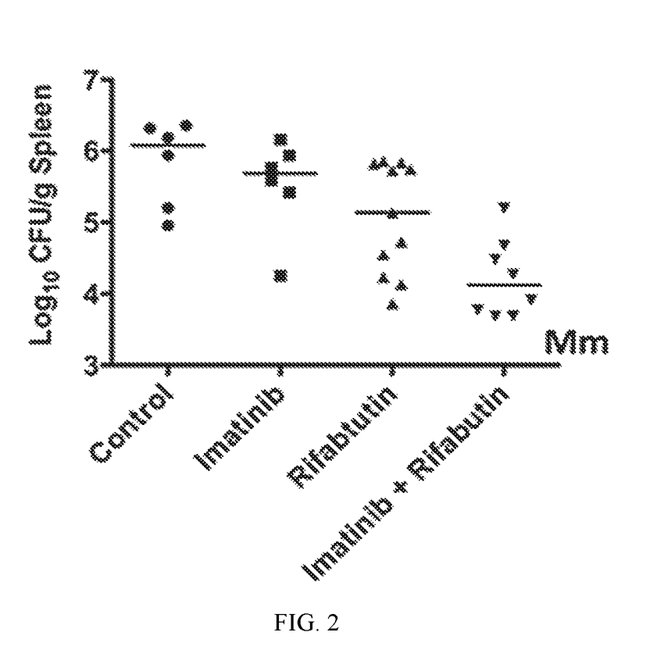
FIG. 2 shows a decrease in bacterial load in mice infected with *mycobacterium* and treated with Gleevec alone, Rifabutin alone, and their combination. The data indicates that a combination therapy of imatinib and antibiotics decreases overall bacterial load. Mice infected with *mycobacterium* were administered 100 mg/kg/day alone, Rifabtutin (2.5 mg/kg/day) alone, and/or a combination of both. CFU in the spleen were determined 7 days (p. i.).
Figure 3A:
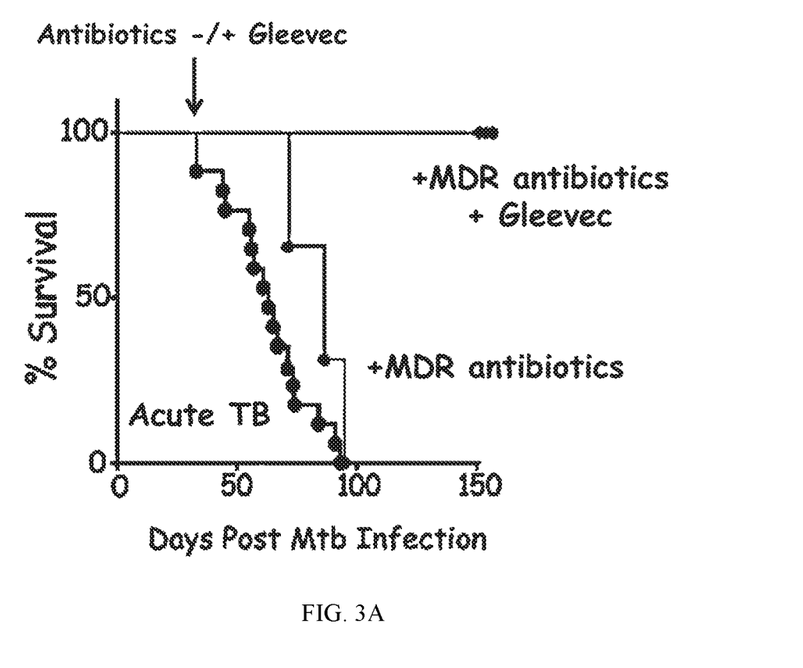
FIG. 3A shows data of experiments with Rhesus macaques for acute TB.

The Rhesus TB model recapitulates the major features of TB infection in humans. Innocula of 100-300 MTb result in an active TB infection, and all animals succumb within three months (FIG. 3A). A low aerosol inoculum (10 CFU) results in a latent infection, which persists. However, a latent infection can be induced to reactivate by various immuosuppresive regiments, including SIV infection, which results in death of 75% of animals within 3 months as a result of an active TB infection. Two experiments were conducted with Gleevec (imatinib mesylate). The dose was chosen to be the lowest that could elicit emergency myelopoiesis in uninfected animals. In the first experiment, the effects of Gleevec was tested against active TB. Six weeks after a receiving an inoculum of 100-300 Mtb, all animals developed active TB. Beginning at this time point, animals were administered daily either placebo, a limited regimen of bacteriostatic antibiotics designed to mimic the current MDR regimen in humans (moxyfloxacine, ethambutol, and pyrazinamide, but not INH or Rif which would kill the antibiotic sensitive Mtb used in this experiment, MDR TB being too dangerous), or antibiotics plus Gleevec. The untreated and antibiotic-treated animals all died within 6 weeks, and all Gleevec/antibiotic-treated animals survived. Bacterial loads upon sacrifice 6-8 weeks later indicated that animals had bacterial loads similar to those observed in latent animals, and only limited inflammation.

Figure 3B:
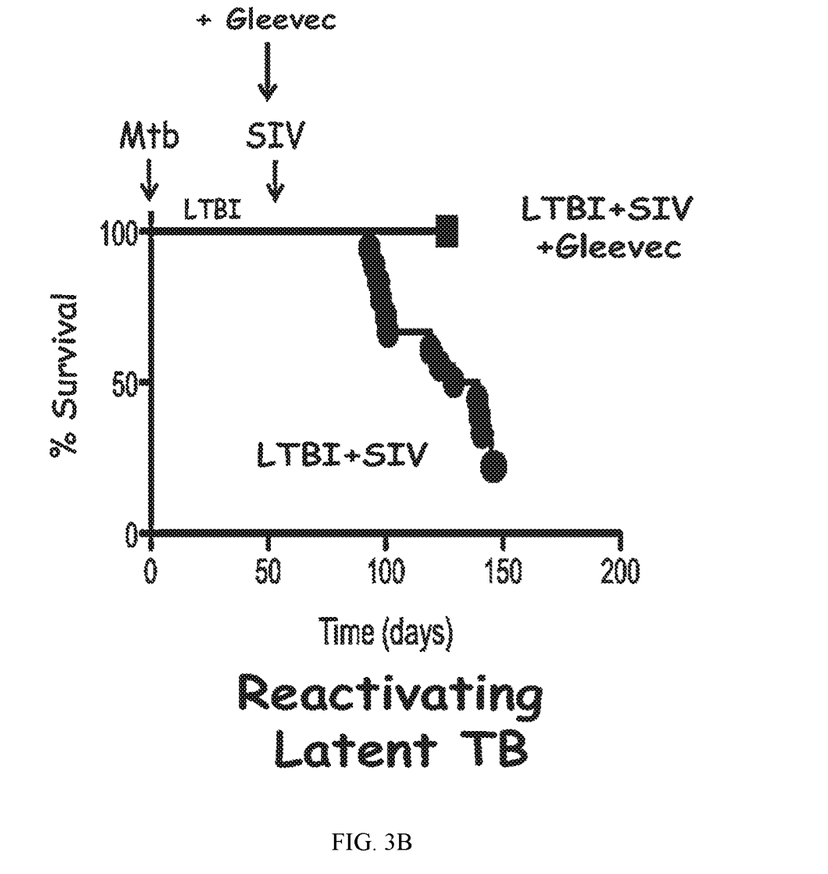
FIG. 3B shows data of experiments with Rhesus macaques for reactivating latent TB.

In a second experiment, animals were given a latent infection for 6-10 weeks, and then administered SIV. At this point animals were administered placebo or Gleevec daily. In 75% of controls, TB reactivation was observed and those animals succumbed, By contrast, all Gleevec-treated animals survived despite having viral loads equivalent to those of controls (FIG. 3B). Together, these data indicate that Gleevec both controls an active TB infection and prevents reactivation induced by SIV.

The invention claimed is:

1. A method of treating tuberculosis comprising administering imatinib in an amount of 50 to 400 mg per day in combination with another antibiotic selected from ethambutol, isoniazid, pyrazinamide, rifabutin, rifampin, rifapentine, amikacin, capreomycin, cycloserine, ethionamide, levofloxacin, moxifloxacin, para-aminosalicylic acid, streptomycin, or combinations thereof, to a human subject in need thereof.

2. The method of claim 1, wherein imatinib is administered in the amount of 50 to 100 mg per day.

3. The method of claim 1, wherein the subject is diagnosed with or exhibiting symptoms of an active tuberculosis infection.

4. A pharmaceutical product comprising a combination of imatinib and an antiviral agent.

5. The pharmaceutical product of claim 4, wherein the antiviral agent is a combination selected from:
   a combination of abacavir and lamivudine;
   a combination of abacavir, dolutegravir, and lamivudine;
   a combination of abacavir, lamivudine, and zidovudine;
   a combination of atazanavir and cobicistat;
   a combination of darunavir and cobicistat;
   a combination of efavirenz, emtricitabine, and tenofovir disoproxil fumarate;
   a combination of elvitegravir, cobicistat, emtricitabine, and tenofovir alafenamide fumarate;
   a combination of elvitegravir, cobicistat, emtricitabine, and tenofovir disoproxil fumarate;
   a combination of emtricitabine, rilpivirine, and tenofovir alafenamide;
   a combination of emtricitabine, rilpivirine, and tenofovir disoproxil fumarate;
   a combination of emtricitabine and tenofovir alafenamide;
   a combination of emtricitabine and tenofovir disoproxil fumarate;
   a combination of lamivudine and zidovudine; and
   a combination of lopinavir and ritonavir.

6. The pharmaceutical product of claim 4, wherein the antiviral agent is a nucleoside reverse transcriptase inhibitor (NRTI) selected from abacavir, didanosine, emtricitabine, lamivudine, stavudine, tenofovir disoproxil fumarate, and zidovudine, or combinations thereof.

7. The pharmaceutical product of claim 4, wherein the antiviral agent is a non-nucleoside reverse transcriptase inhibitor (NNRTI) selected from efavirenz, etravirine, nevirapine, and rilpivirine, or combinations thereof.

8. The pharmaceutical product of claim 4, wherein the antiviral agent is a protease inhibitor selected from atazanavir, darunavir, fosamprenavir, indinavir, nelfinavir, ritonavir, saquinavir, and tipranavir, or combinations thereof.

9. A method of treating or preventing tuberculosis comprising administering imatinib to a human subject in need thereof diagnosed with HIV.

10. The method of claim 9 wherein imatinib is administered in combination with an antiviral agent.

11. The method of claim 10 wherein the antiviral agent is a combination selected from:
    a combination of abacavir and lamivudine;
    a combination of abacavir, dolutegravir, and lamivudine;
    a combination of abacavir, lamivudine, and zidovudine;
    a combination of atazanavir and cobicistat;
    a combination of darunavir and cobicistat;
    a combination of efavirenz, emtricitabine, and tenofovir disoproxil fumarate;
    a combination of elvitegravir, cobicistat, emtricitabine, and tenofovir alafenamide fumarate;
    a combination of elvitegravir, cobicistat, emtricitabine, and tenofovir disoproxil fumarate;
    a combination of emtricitabine, rilpivirine, and tenofovir alafenamide;
    a combination of emtricitabine, rilpivirine, and tenofovir disoproxil fumarate;
    a combination of emtricitabine and tenofovir alafenamide;
    a combination of emtricitabine and tenofovir disoproxil fumarate;
    a combination of lamivudine and zidovudine; and
    a combination of lopinavir and ritonavir.

12. The method of claim 9, wherein imatinib is administered in the amount of 50 to 400 mg per day.

13. The method of claim 9, wherein imatinib is administered in the amount of 50 to 100 mg per day.

14. A method of preventing reactivation of a latent tuberculosis infection comprising administering imatinib in an amount of 50 to 400 mg per day to a human subject in need thereof, wherein administration prevents reactivation of a latent tuberculosis infection.

15. A method of treating tuberculosis comprising administering imatinib in an amount of 50 to 400 mg per day to a human subject in need thereof, wherein the subject is resistant to treatment of tuberculosis with rifampicin.

16. The method of claim 15, wherein imatinib is administered in the amount of 50 to 100 mg per day.

17. The method of claim 15, wherein the subject is diagnosed with or exhibiting symptoms of an active tuberculosis infection.

18. A method of treating tuberculosis comprising administering imatinib in an amount of 50 to 400 mg per day in combination with bedaquiline to a human subject in need thereof.

19. A method of treating tuberculosis comprising administering imatinib in an amount of 50 to 400 mg per day in combination with delamanid to a human subject in need thereof.

* * * * *